(12) United States Patent
Nakajima et al.

(10) Patent No.: US 10,048,087 B2
(45) Date of Patent: Aug. 14, 2018

(54) MEASUREMENT APPARATUS, MEASUREMENT METHOD AND NON-TRANSITORY COMPUTER READABLE RECORDING MEDIUM WITH PROGRAM STORED THEREON

(71) Applicant: CASIO COMPUTER CO., LTD., Shibuya-ku, Tokyo (JP)

(72) Inventors: Mitsuyasu Nakajima, Tokyo (JP); Ryohei Yamamoto, Tokyo (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 384 days.

(21) Appl. No.: 14/839,641

(22) Filed: Aug. 28, 2015

(65) Prior Publication Data
US 2016/0061859 A1 Mar. 3, 2016

(30) Foreign Application Priority Data
Sep. 2, 2014 (JP) .................. 2014-177898

(51) Int. Cl.
*G01P 15/00* (2006.01)
*G01C 22/00* (2006.01)
(Continued)

(52) U.S. Cl.
CPC ............ *G01C 22/006* (2013.01); *A61B 5/112* (2013.01); *A61B 5/1123* (2013.01);
(Continued)

(58) Field of Classification Search
CPC .............................. G01C 21/12; G01C 22/006
See application file for complete search history.

(56) References Cited

U.S. PATENT DOCUMENTS 4,578,769 A * 3/1986 Frederick ................. A43B 3/00
 234/105
4,736,312 A * 4/1988 Dassler ................ A43B 3/0005
 235/105
(Continued)

FOREIGN PATENT DOCUMENTS

CN 103308068 A 9/2013
JP 2003302419 A 10/2003
(Continued)

OTHER PUBLICATIONS

Chinese Office Action (and English translation thereof) dated Jun. 20, 2017 issued in counterpart Chinese Application No. 201510557530.0.

*Primary Examiner* — Elias Desta
(74) *Attorney, Agent, or Firm* — Holtz, Holtz & Volek PC (57) ABSTRACT

A measurement apparatus including: a first sensor which continuously acquires a vertical direction acceleration generated in accordance with a traveling movement of a user, a second sensor which continuously acquires a travel direction acceleration generated in accordance with the traveling movement, a first determination unit which determines, based on a continuous change of the vertical direction acceleration and the travel direction acceleration, a plurality of landing points of time each being a point of time when a foot of the user lands, and a first acquiring unit which acquires, based on the plurality of landing points of time, a period required for one step of the user in the traveling movement.

13 Claims, 7 Drawing Sheets

(51) Int. Cl.
  *A61B 5/11*   (2006.01)
  *G01C 21/12*  (2006.01)

(52) U.S. Cl.
  CPC .......... *A61B 5/1126* (2013.01); *G01C 21/12* (2013.01); *A61B 2562/0219* (2013.01)

(56) References Cited

U.S. PATENT DOCUMENTS

| | | | |
|---|---|---|---|
| 5,899,963 A * | 5/1999 | Hutchings | A43B 3/0005 700/14 |
| 6,813,582 B2 * | 11/2004 | Levi | G01C 21/12 701/495 |
| 6,820,002 B2 | 11/2004 | Terada | |
| 7,353,986 B2 | 4/2008 | Sugai | |
| 8,712,508 B2 | 4/2014 | Izumida et al. | |
| 2013/0245470 A1 * | 9/2013 | Izumida | A61B 5/1123 600/509 |

FOREIGN PATENT DOCUMENTS

| | | | |
|---|---|---|---|
| JP | 2005267152 A | 9/2005 |
| JP | 2011090548 A | 5/2011 |
| JP | 2011163861 A | 8/2011 |
| JP | 2012179114 A | 9/2012 |
| JP | 2013160657 A | 8/2013 |

* cited by examiner

MEASUREMENT APPARATUS, MEASUREMENT METHOD AND NON-TRANSITORY COMPUTER READABLE RECORDING MEDIUM WITH PROGRAM STORED THEREON

CROSS-REFERENCE TO RELATED APPLICATIONS

The entire disclosure of Japanese Patent Application No. 2014-177898 filed on Sep. 2, 2014 including description, claims, drawings, and abstract are incorporated herein by reference in its entirety.

BACKGROUND OF THE INVENTION

1. Field of the Invention

The present invention relates to a measurement apparatus, a measurement method and a non-transitory computer readable recording medium with a program stored thereon.

2. Description of Related Art

Conventionally, there have been known various techniques to analyze traveling movements such as a walking movement and a running movement by using acceleration sensors (for example, refer to Japanese Patent Application Laid Open Publication No. 2005-267152). Basic information necessary for the analysis of movements includes a period of time required for one step in the traveling movements.

For example, there is a technique to calculate a synthesis acceleration of acceleration data detected by a triaxial acceleration sensor and calculate the period required for one step from a relationship between the calculated synthesis acceleration and the number of steps corresponding to the number of arm swings when a user walks holding a mobile terminal with the triaxial acceleration sensor mounted thereon (for example, refer to Japanese Patent Application Laid Open Publication No. 2011-090548).

However, in a case of running movement, the output value of the axis corresponding to the direction of gravity acceleration is relatively large and thus dominant even when the synthesis acceleration is obtained by summing up the triaxial acceleration data as in the Japanese Patent Application Laid Open Publication No. 2011-090548. Thus, there is a problem that the accuracy of the period required for one step which is calculated by using the synthesis acceleration is lowered when the user runs faster.

SUMMARY OF THE INVENTION

According to one aspect of the present invention, there is provided a measurement apparatus including: a first sensor which continuously acquires a vertical direction acceleration generated in accordance with a traveling movement of a user, a second sensor which continuously acquires a travel direction acceleration generated in accordance with the traveling movement, a first determination unit which determines, based on a continuous change of the vertical direction acceleration and the travel direction acceleration, a plurality of landing points of time each being a point of time when a foot of the user lands, and a first acquiring unit which acquires, based on the plurality of landing points of time, a period required for one step of the user in the traveling movement.

According to another aspect of the present invention, there is provided a measurement method including: acquiring continuously a vertical direction acceleration generated in accordance with a traveling movement of a user, acquiring continuously a travel direction acceleration generated in accordance with the traveling movement, determining, based on a continuous change of the acquired vertical direction acceleration and the travel direction acceleration, a plurality of landing points of time each being a point of time when a foot of the user lands, and acquiring, based on the plurality of landing points of time, a period required for one step of the user in the traveling movement.

According to another aspect of the present invention, there is provided a non-transitory computer readable recording medium which stores an executable program that is read by a computer to make a controlling unit execute a following procedure, the procedure including: acquiring continuously a vertical direction acceleration generated in accordance with a traveling movement of a user, acquiring continuously a travel direction acceleration generated in accordance with the traveling movement, determining, based on a continuous change of the acquired vertical direction acceleration and the travel direction acceleration, a plurality of landing points of time each being a point of time when a foot of the user lands, and acquiring, based on the plurality of landing points of time, a period required for one step of the user in the traveling movement.

BRIEF DESCRIPTION OF THE DRAWINGS

The above and other objects, advantages and features of the present invention will become more fully understood from the detailed description given hereinafter and the appended drawings which are given by way of illustration only, and thus are not intended as a definition of the limits of the present invention, and wherein.

DETAILED DESCRIPTION OF THE PREFERRED EMBODIMENT

Hereinafter, a specific embodiment of the present invention will be described by using the drawings. However, the scope of the invention is not limited to the illustrated examples.

Figure 1:
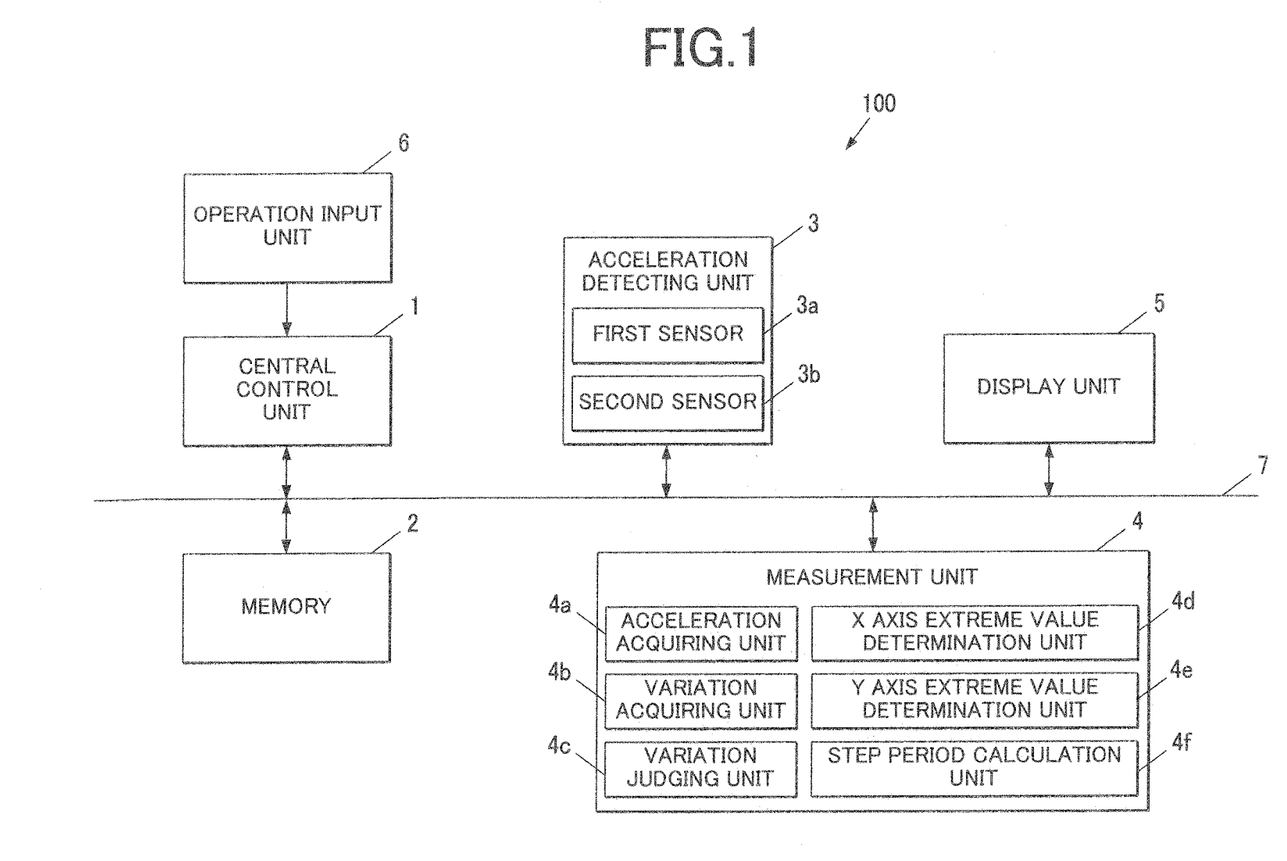
FIG. 1 is a block diagram showing a schematic configuration of a measurement apparatus in an embodiment to which the present invention is applied.
Figure 2:
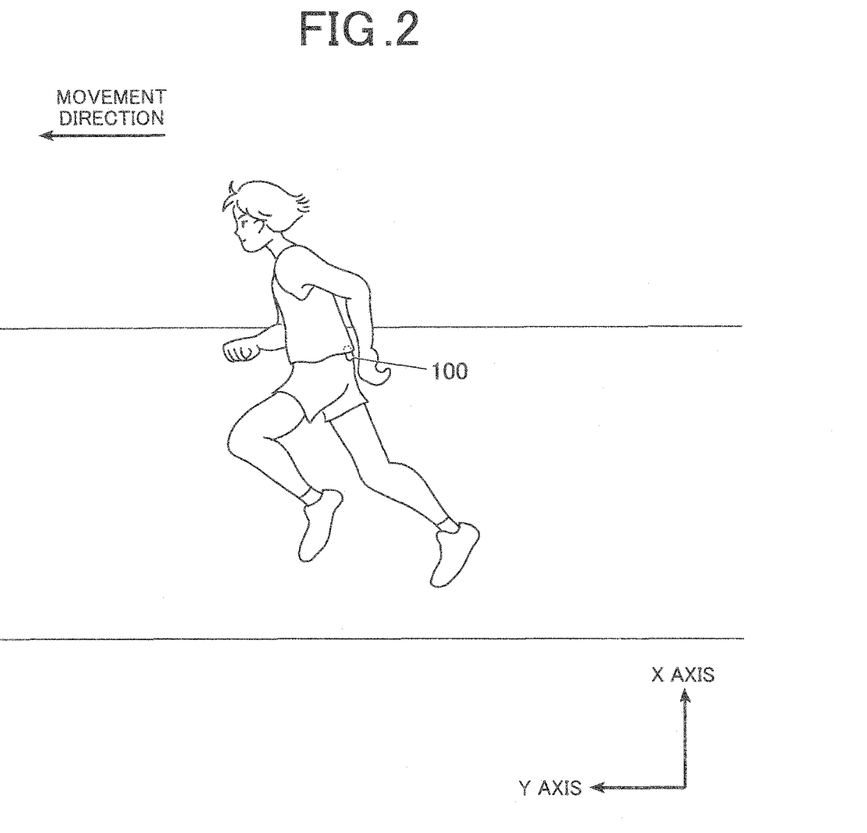
FIG. 2 is a view schematically showing a state in which a user wears the measurement apparatus of FIG. 1.

FIG. 1 is a block diagram showing a schematic configuration of a measurement apparatus 100 in an embodiment to which the present invention is applied. FIG. 2 is a view schematically showing a traveling movement of a user wearing the measurement apparatus 100 around the waist.

As shown in FIG. 1, the measurement apparatus 100 in the embodiment includes a central control unit 1, a memory 2, an acceleration detecting unit 3, a measurement unit 4, a display unit 5 and an operation input unit 6.

The central control unit 1, the memory 2, the acceleration detecting unit 3, the measurement unit 4 and the display unit 5 are connected to each other via a bus line 7.

As shown in FIG. 2, the measurement apparatus 100 can be worn on a predetermined position such as waist of the user performing a traveling movement such as a walking movement and a running movement, for example. The measurement apparatus 100 is worn by a user so that the X axis direction of the acceleration detecting unit 3 is nearly parallel to the vertical direction and the Y axis direction of the acceleration detecting unit 3 is nearly parallel to the travel direction (movement direction) of the user as will hereinafter be described in detail. In the embodiment, when the acceleration detecting unit 3 is worn by the user, the acceleration detecting unit 3 detects an upward acceleration in the vertical direction as a positive value and detects an acceleration directed from the back side toward the stomach side of the user in the travel direction as a positive value.

The central control unit 1 controls the units of the measurement apparatus 100. Specifically, for example, the central control unit 1 includes a CPU (Central Processing Unit), a RAM (Random Access Memory) and a ROM (Read Only Memory) not shown in the drawings, and performs various control operations in accordance with various processing programs (not shown in the drawings) for the measurement apparatus 100 stored in the ROM. At this time, the CPU stores various processing results in storage areas in the RAM and displays the processing results on the display unit 5 as needed.

The RAM includes a program storage area for loading processing programs to be executed by the CPU, a data storage area for storing input data and processing results generated when the processing programs are executed, and such like.

The ROM stores programs stored in a form of computer readable program code, specifically, system programs executable in the measurement apparatus 100, various processing programs executable by the system programs, data used when the various processing programs are executed, and such like.

The memory 2 is formed of a DRAM (Dynamic Random Access Memory), for example, and temporarily stores data and such like which are processed by the central control unit 1, the acceleration detecting unit 3, the measurement unit 4 and the display unit 5.

The acceleration detecting unit 3 detects the above-mentioned accelerations in the X axis direction and the Y axis direction.

That is, the acceleration detecting unit 3 includes a biaxial acceleration sensor (not shown in the drawings) which detects respective accelerations in the two directions orthogonal to each other, and the respective accelerations in the X and Y axis directions are detected by using the sensor. Specifically, the acceleration detecting unit 3 includes a first sensor 3a and a second sensor 3b.

The first sensor 3a detects continuously an acceleration in the vertical direction which is generated in accordance with the traveling movement of the user.

Figure 6A:
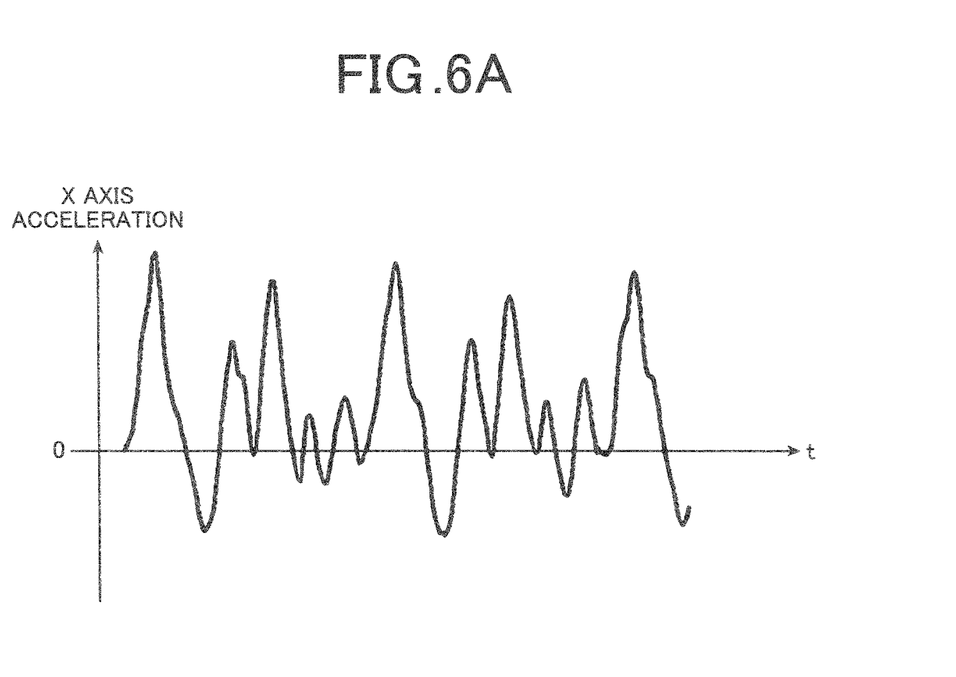
FIG. 6A is a view which schematically shows an example of an output waveform of an acceleration sensor in the measurement apparatus of FIG. 1.

Specifically, for example, the biaxial acceleration sensor is arranged with the X axis direction thereof nearly parallel to the vertical direction (see FIG. 2), and performs detection by detecting an upward vertical acceleration as a positive value. The first sensor 3a detects the vertical direction acceleration constantly or at predeterminate time intervals and samples the detected signal at a predetermined frequency (200 Hz, for example) to acquire the sampled data as X axis acceleration data ACCX (see FIG. 6A).

The second sensor 3b detects continuously an acceleration in the travel direction generated in accordance with the traveling movement of the user.

Figure 6B:
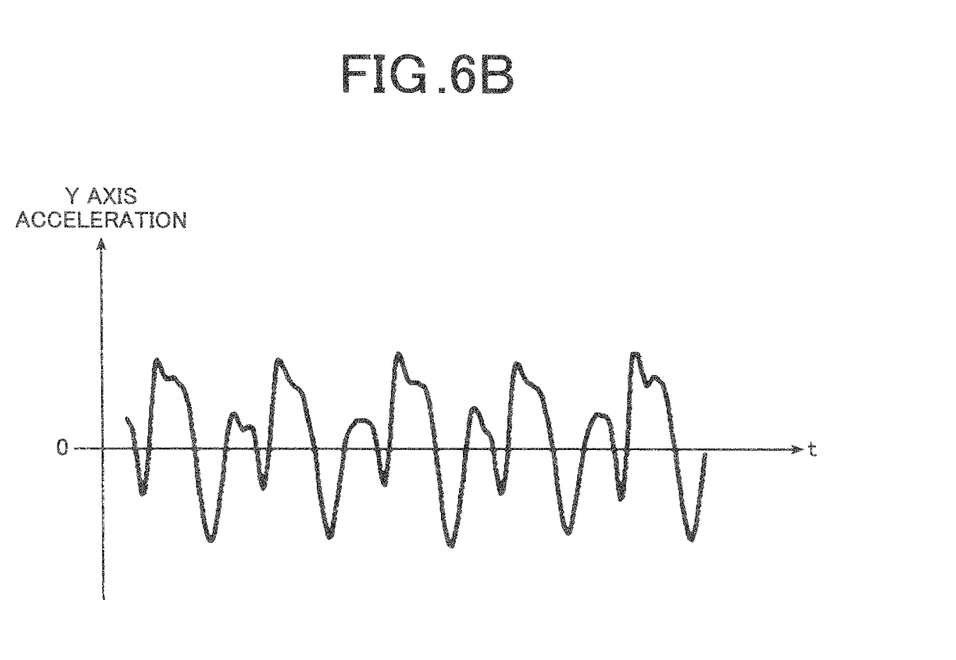
FIG. 6B is a view which schematically shows an example of an output waveform of an acceleration sensor in the measurement apparatus of FIG. 1.

Specifically, for example, the biaxial acceleration sensor is arranged so that the Y axis direction thereof is nearly parallel to the user's travel direction of the traveling movement and the positive direction of the Y axis direction thereof is the direction from the rear side toward the front side of the user (see FIG. 2). The second sensor 3b detects the travel direction acceleration constantly or at predetermined time intervals, samples the detected signal at a predetermined frequency (200 Hz, for example), and acquires the sampled data as Y axis acceleration data ACCY (see FIG. 6B).

The acceleration detecting unit 3 may output, to the memory 2, the X axis acceleration data ACCX and the Y axis acceleration data ACCY which are respectively acquired by the first sensor 3a and the second sensor 3b at each time point of sampling so as to be associated with each other.

The measurement unit 4 includes an acceleration acquiring unit 4a, a variation acquiring unit 4b, a variation judging unit 4c, an X axis extreme value determination unit 4d, a Y axis extreme value determination unit 4e and a step period calculation unit 4f.

For example, each of the units in the measurement unit 4 is formed of a logic circuit; however, the configuration is an example, and the present invention is not limited to this.

The acceleration acquiring unit 4a acquires the acceleration detected by the acceleration detecting unit 3.

Specifically, the acceleration acquiring unit 4a acquires X axis acceleration data ACCX for the amount of predetermined time (1 second, for example) detected by the first sensor 3a in the acceleration detecting unit 3 and Y axis acceleration data ACCY for the amount of predetermined time (1 second, for example) detected by the second sensor 3b which are temporarily stored in the memory 2, by reading out the data from the memory 2, for example.

The variation acquiring unit 4b acquires the change in the travel direction acceleration.

That is, the variation acquiring unit 4b calculates and acquires the change in travel direction acceleration detected by the second sensor 3b in the acceleration detecting unit 3. Specifically, the variation acquiring unit 4b determines the maximum value and the minimum value of the acceleration in the Y axis acceleration data ACCY (waveform data) for the amount of predetermined time (1 second, for example) acquired by the acceleration acquiring unit 4a, and calculates the difference therebetween. The variation acquiring unit 4b acquires the calculated difference between the maximum value and the minimum value as the change in travel direction acceleration.

The above acquiring method of the change in travel direction acceleration is an example, and the present invention is not limited to this. Modification can be appropriately made arbitrarily.

The variation judging unit 4c judges whether the change in travel direction acceleration acquired by the variation acquiring unit 4b is larger than a predetermined judgment value.

Here, the predetermined judgment value is empirically obtained in order to judge whether the traveling movement is a walking movement or a running movement by using the change in travel direction acceleration (for example, the difference between the maximum and minimum values of the acceleration). That is, the predetermined judgment value is adjusted so that, when the traveling movement is a walking movement, the change in the travel direction acceleration is equal to or less than the predetermined judgment value since the change in the travel direction acceleration is relatively small, and on the other hand, when the traveling movement is a running movement, the change in travel direction acceleration is larger than the predetermined judgment value since the change in travel direction acceleration is relatively large.

The X axis extreme value determination unit 4d determines a point of time (taking extreme value point of time) when the vertical direction acceleration takes an extreme value.

That is, the X axis extreme value determination unit 4d determines the point of time when the acceleration takes an extreme value (for example, a point of time t1 when the acceleration takes a local maximum) based on the continuous change of the vertical direction acceleration detected by the first sensor 3a in the acceleration detecting unit 3.

Specifically, for example, if the variation judging unit 4c judges that the change in the travel direction acceleration is larger than the predetermined judgment value, the X axis extreme value determination unit 4d performs smoothing by using a low-pass filter with respect to the X axis acceleration data ACCX (waveform data) for the amount of the predetermined time (1 second, for example) acquired by the acceleration acquiring unit 4a. Then, in the smoothed X axis acceleration data ACCX, the X axis extreme value determination unit 4d determines points of time (taking positive slope point of time) t0 when the waveform takes a "positive" slope and the acceleration is a predetermined reference value th1 (see FIG. 7A). Here, the predetermine reference value th1 is empirically obtained in consideration of gravity acceleration, for example.

Figure 7A:
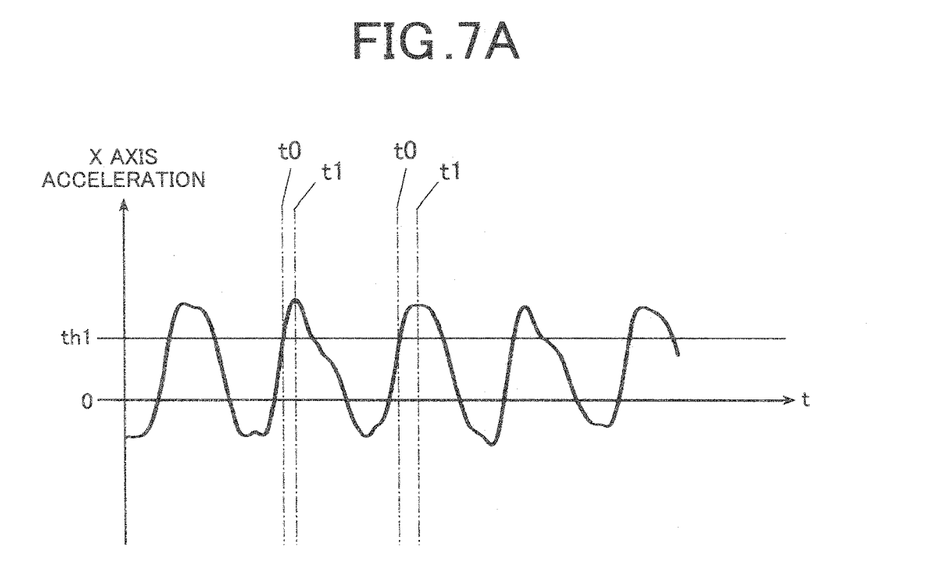
FIG. 7A is a view which schematically shows an example of an output waveform of an acceleration sensor in the measurement apparatus of FIG. 1.

With respect to each of the plurality of determined points of time t0 in the smoothed X axis acceleration data ACCX, the X axis extreme value determination unit 4d searches along the waveform toward the positive direction of the time axis from the point of time t0 and determines the point of time t1 when the acceleration takes a local maximum. In the running movement, there is a point of time t1 when an upward acceleration takes a maximum value in the early phase of landing period when a foot of the user lands since the running movement has relatively large vertical movement of body. Depending on conditions such as a smoothing method, there could be two or more local maximums within an interval between adjacent two points of time t0. In such case, the desired point of time t1 may be the point of time corresponding to the largest local maximum among the plurality of local maximums within a predetermined period of time from the point of time t0 (for example, a period of time which is approximately ¼ to ⅕ of the interval between the adjacent points of time t0).

The acceleration detecting unit 3 may detect an upward acceleration in the vertical direction as a negative value when the acceleration detecting unit 3 is worn by the user. In such case, the positive and negative signs of values detected by the acceleration detecting unit 3 merely needs to be reversed.

The Y axis extreme value determination unit 4e determines a point of time (landing point of time) when the travel direction acceleration takes an extreme value.

That is, the Y axis extreme value determination unit 4e determines the point of time when a foot of the user landed based on the continuous change of the vertical direction acceleration detected by the first sensor 3a in the acceleration detecting unit 3 and the travel direction acceleration detected by the second sensor 3b. Specifically, when the change judgment unit 4c judges that the change in the travel direction acceleration is larger than a predetermined judgment value, the Y axis extreme value determination unit 4e determines the point of time when the travel direction acceleration detected by the second sensor 3b takes an extreme value (for example, the point of time t2 when the acceleration takes a local minimum) as the point of time when a foot of the user landed based on the continuous change of vertical direction acceleration detected by the first sensor 3a (more specifically, based on the point of time t1 when the acceleration takes a local maximum, the point of time t1 being determined by the X axis extreme value determination unit 4d).

Figure 7B:
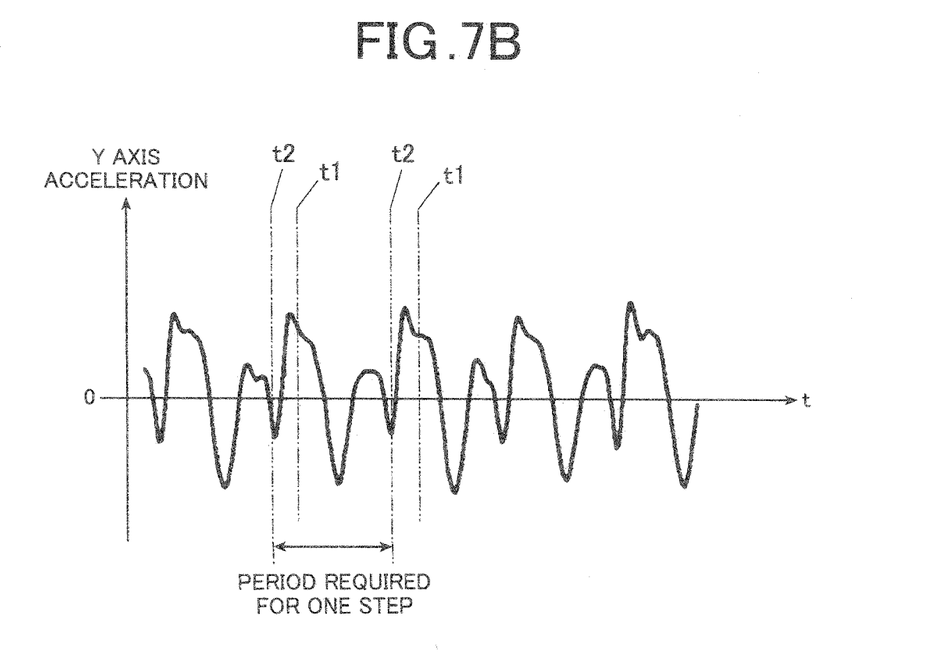
FIG. 7B is a view which schematically shows an example of an output waveform of an acceleration sensor in the measurement apparatus of FIG. 1.

For example, with respect to each of the plurality of points of time t1 when the acceleration takes a local maximum, the point of time t1 being determined by the X axis extreme value determination unit 4d, in the Y axis acceleration data ACCY (waveform data) for the amount of predetermined time (for example, 1 second) acquired by the acceleration acquiring unit 4a, the Y axis extreme value determination unit 4e searches toward the negative direction of time axis from each of the points of time t1, and determines the point of time t2 (point of time when a foot of the user landed) when the travel direction acceleration value is "negative" and the acceleration value takes a local minimum for the first time (see FIG. 7B). In a running movement, a point of time t2 when the travel direction acceleration takes a local minimum exists for each step since the running movement repeats the operation of bringing a force toward the opposite direction to the travel direction due to the landing of each left and right foot and thereafter increasing the travel direction acceleration. Here, as shown in FIG. 7B, since there are a plurality of negative local minimums of acceleration within an interval between adjacent two points of time t1, it is not possible to determine the local minimum corresponding to the point of time when a foot of the user landed only by the Y axis acceleration data ACCY (waveform data). As in the embodiment, the point of time corresponding to the point of time when a foot of the user landed can be determined by referring to the X axis acceleration data ACCX in addition to the Y axis acceleration data ACCY.

The acceleration detecting unit 3 may detect a travel direction acceleration directed from the back side to the stomach side of the user as a negative value when the acceleration detecting unit 3 is worn by the user. In such case, positive and negative signs of values detected by the acceleration detecting unit 3 merely needs to be reversed.

The step period calculation unit 4f calculates the period required for one step in the movement.

That is, the step period calculation unit 4f calculates and acquires the period required for one step in the traveling movement based on the point of time when the travel direction acceleration takes an extreme value (for example, point of time t2 when the acceleration takes a local minimum) which was determined as the point of time when a foot of the user landed by the Y axis extreme value determination unit 4e. Specifically, if the change judgment unit 4c judges that the change in the travel direction acceleration is larger than the predetermined judgment value, in the running state processing (see FIG. 4), the step period calculation unit 4f calculates each of the points of time t2 as a "step boundary" and each time interval between adjacent two points of time t2 as a period required for one step in the running movement, each of the points of time t2 being determined by the Y axis extreme value determination unit 4e and being a point of time when the travel direction acceleration takes a local minimum.

If the variation judging unit 4c judges that the change in the travel direction acceleration is not larger than the predetermined judgment value (the change is equal to or less than the judgment value), in the walking state processing (see FIG. 5), the step period calculation unit 4f calculates the period required for one step in the walking movement based on continuous change of the vertical direction acceleration detected by the first sensor 3a of the acceleration detecting unit 3. Specifically, for example, the step period calculation unit 4f performs smoothing using a low-pass filter with respect to the X axis acceleration data ACCX (waveform data) for the amount of predetermined time (for example, 1 second) acquired by the acceleration acquiring unit 4a. The step period calculation unit 4f determines, as a "step boundary", the point of time when the waveform has a "positive" slope and the acceleration is the predetermined reference value in the smoothed X axis acceleration data ACCX. Here, the predetermined reference value is empirically obtained in consideration of gravity acceleration and such like.

Figure 5:
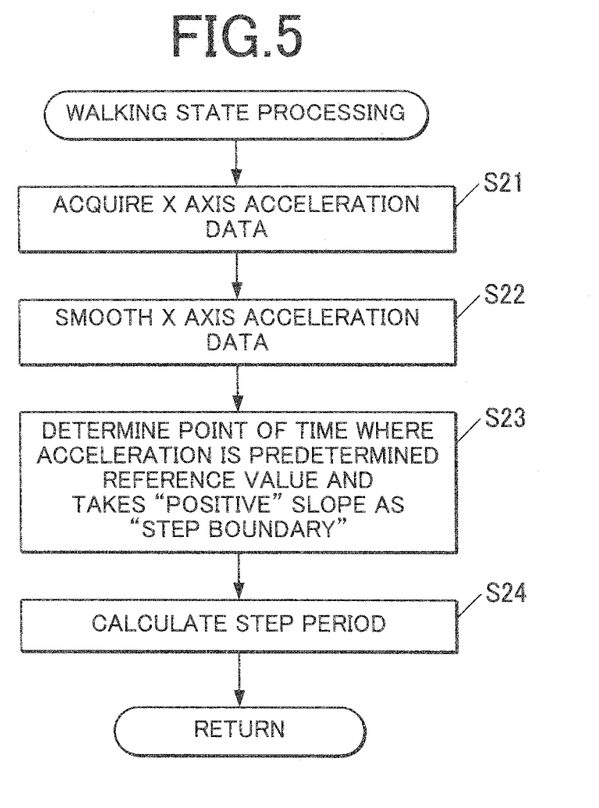
FIG. 5 is a flowchart showing an example of an operation according to walking state processing in the measurement processing of FIG. 3.

The step period calculation unit 4f calculates a time interval between the determined adjacent two points of time as a period required for one step in the walking movement.

The display unit 5 is configured by including a light emitting diode, what is called a seven-segment type liquid crystal display panel and such like, and notifies various types of information. Specifically, the display unit 5 displays the acceleration detected by the acceleration detecting unit 3 and the period required for one step in the movement measured by the measurement unit 4, for example.

The operation input unit 6 is configured by including data input keys for inputting numbers and characters, up, down, left and right shift keys for selecting data and performing scrolling, various function keys and such like. The operation input unit 6 outputs a pressing signal of a key pressed down by a user to the CPU of the central control unit 1.

The operation input unit 6 may have a configuration in which a touch panel (not shown in the drawings) is disposed on the display screen of the display unit 5 to input various types of instructions according to the touched position of the touch panel.

<Measurement Processing>

Next, measurement processing by the measurement apparatus 100 will be described with reference to FIGS. 3 to 7.

Figure 3:
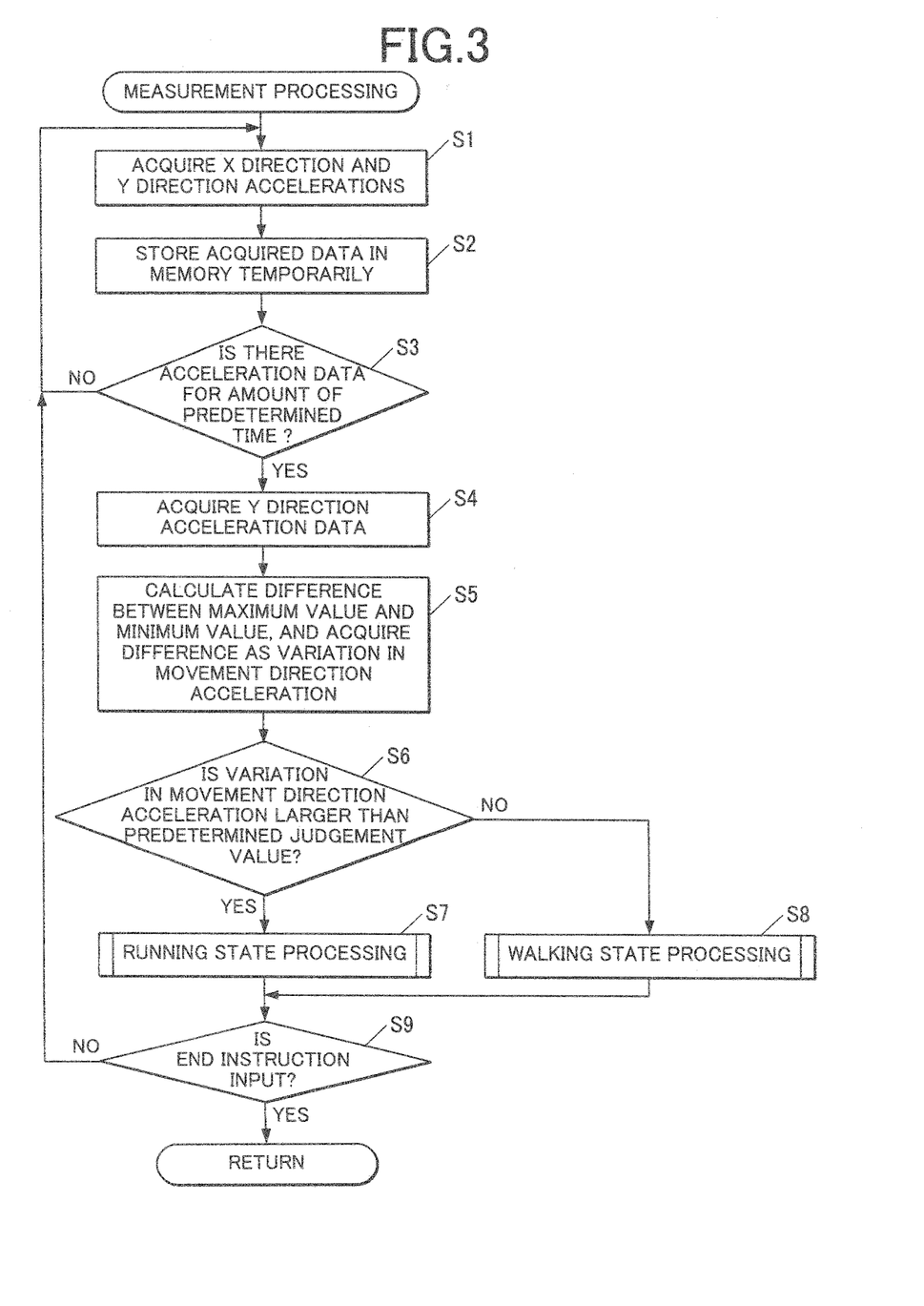
FIG. 3 is a flowchart showing an example of an operation according to measurement processing by the measurement apparatus of FIG. 1.

FIG. 3 is a flowchart showing an example of operation according to the measurement processing.

The measurement apparatus 100 is worn by a user so that the X axis direction of the acceleration detecting unit 3 is nearly parallel to the vertical direction and the Y axis direction thereof is nearly parallel to the user's travel direction. When worn by the user, the acceleration detecting unit 3 detects an upward vertical direction acceleration as a positive value, and detects a travel direction acceleration directed from a back side toward a stomach side of the user as a positive value. The measurement processing is performed at every sampling period of acceleration data by the acceleration detecting unit 3.

As shown in FIG. 3, first, when the user performs a movement, the acceleration detecting unit 3 detects respective accelerations in X and Y axis directions at a predetermined sampling period by using the biaxial acceleration sensor (step S1). Specifically, the first sensor 3a detects the vertical direction acceleration and samples the detected signal at a predetermined frequency (for example, 200 Hz) to acquire data as the X axis acceleration data ACCX (see FIG. 6A). The second sensor 3b detects the travel direction acceleration and samples the detected signal at a predetermined frequency (for example, 200 Hz) to acquire data as the Y axis acceleration data ACCY (see FIG. 6B).

The acceleration detecting unit 3 outputs the acquired X axis acceleration data ACCX and Y axis acceleration data ACCY to the memory 2 so as to be associated with each other. The memory 2 temporarily stores the X axis acceleration data ACCX and the Y axis acceleration data ACCY in a temporary storage area which is formed of a ring buffer, for example (step S2).

The X axis acceleration data ACCX and Y axis acceleration data ACCY for the amount of 2 seconds can be stored in the temporary storage area of the memory 2, for example.

Next, the measurement unit 4 determines whether X axis acceleration data ACCX and Y axis acceleration data ACCY for the amount of predetermined time (for example, 1 second) are stored in the temporary storage area of the memory 2 (step S3).

Here, if it is not determined that the X axis acceleration data ACCX and Y axis acceleration data ACCY for the amount of predetermined time (for example, 1 second) are stored (step S3; NO), the CPU of the central control unit 1 returns the processing to step S1, and the acceleration detecting unit 3 detects respective accelerations in the X and Y axis directions at the predetermined sampling period.

On the other hand, if it is determined that the X axis acceleration data ACCX and Y axis acceleration data ACCY for the amount of predetermined time (for example, 1 second) are stored (step S3; YES), the acceleration acquiring unit 4a reads out and acquires the latest Y axis acceleration data ACCY for the amount of predetermined time from the memory 2 (step S4). For example, when the sampling frequency is 200 Hz and the predetermined time is 1 second, the acceleration acquiring unit 4a acquires the continuous change of Y axis acceleration data ACCY for the amount of 200 pieces.

The variation acquiring unit 4b calculates the difference between the maximum value and the minimum value of acceleration in the Y axis acceleration data for the amount of predetermined time acquired by the acceleration acquiring unit 4a, and acquires the calculated difference between the maximum and minimum value as the change in the travel direction acceleration (step S5).

Next, the variation judging unit 4c judges whether the change in travel direction acceleration acquired by the variation acquiring unit 4b is larger than the predetermined judgment value (step S6).

Here, if it is judged that the change in travel direction acceleration is larger than the predetermined judgment value (step S6; YES), the traveling movement is running movement, and the measurement unit 4 performs running state processing (see FIG. 4) (step S7; to be described in detail later). On the other hand, if it is not judged that the change in travel direction acceleration is larger than the predetermined judgment value (step S6; NO), the traveling movement is walking movement, and the measurement unit 4 performs walking state processing (see FIG. 5) (step S8; to be described in detail later).

Thereafter, the CPU of the central control unit 1 judges whether the end instruction is input based on a predetermined operation on the operation input unit 6 by the user (step S9).

Here, if it is not judged that the end instruction is input (step S9; NO), the CPU of the central control unit 1 returns the processing to step S1 and controls execution of the above each processing.

On the other hand, if it is judged that the end instruction is input (step S9; YES), the CPU of the central control unit 1 ends the measurement processing.

<Running State Processing>

Next, the running state processing in the measurement processing will be described with reference to FIG. 4.

Figure 4:
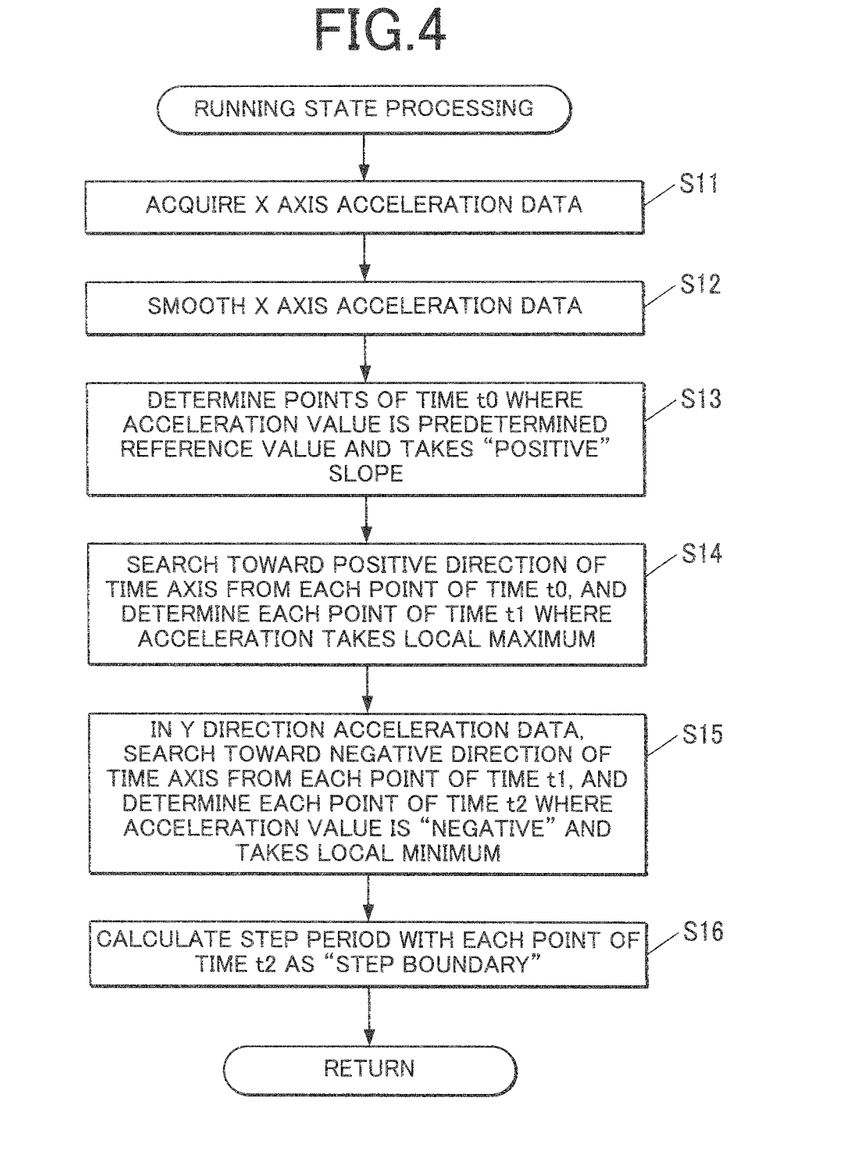
FIG. 4 is a flowchart showing an example of an operation according to running state processing in the measurement processing of FIG. 3.

FIG. 4 is a flowchart showing an example of operation according to the running state processing.

As shown in FIG. 4, first, the acceleration acquiring unit 4a reads out and acquires the latest X axis acceleration data ACCX for the amount of predetermined time (for example, 1 second) corresponding to the Y axis acceleration data ACCY which has been acquired from the memory 2 (step S11).

Next, the X axis extreme value determination unit 4d performs smoothing using the low-pass filter with respect to the X axis acceleration data ACCX acquired by the acceleration acquiring unit 4a (step S12). The X axis extreme value determination unit 4d determines points of time t0 when the acceleration value is the reference value th1 and the waveform has a "positive" slope in the smoothed X axis acceleration data ACCX (step S13; see FIG. 7A). With respect to the plurality of determined points of time t0, the X axis extreme value determination unit 4d searches toward the positive direction of time axis from each of the points of time t0 and determines the point of time t1 when the vertical direction acceleration takes a local maximum (step S14; see FIG. 7A).

Next, in the Y axis acceleration data ACCY for the amount of predetermined time (for example, 1 second), with respect to the plurality of the points of time t1 when the acceleration takes a local maximum determined by the X axis extreme value determination unit 4d, the Y axis extreme value determination unit 4e searches toward the negative direction of time axis from each of the points of time t1 and determines the point of time t2 when the travel direction acceleration value is "negative" and the acceleration takes a local minimum (step S15; see FIG. 7B).

Based on each of the points of time t2 when the travel direction acceleration takes a local minimum, each of the points of time t2 being determined by the Y axis extreme value determination unit 4e as a "step boundary", the step period calculation unit 4f calculates a time interval between adjacent two points of time t2 as a period required for one step in the running movement (step S16; see FIG. 7B).

The calculated period required for one step in the running movement may be stored in a storage unit (for example, memory 2).

<Walking State Processing>

Next, the walking state processing in the measurement processing will be described with reference to FIG. 5.

FIG. 5 is a flowchart showing an example of operation according to the walking state processing.

As shown in FIG. 5, first, the acceleration acquiring unit 4a reads out and acquires the latest X axis acceleration data ACCX for the amount of predetermined time (for example, 1 second) from the memory 2 (step S21).

The step period calculation unit 4f performs smoothing using the low-pass filter with respect to the X axis acceleration data ACCX for the amount of predetermined time acquired by the acceleration acquiring unit 4a (step S22). The step period calculation unit 4f determines, as a "step boundary", the points of time when the acceleration value is the predetermined reference value and the waveform takes a "positive" slope in the smoothed X axis acceleration data ACCX (step S23).

The step period calculation unit 4f calculates a time interval between the determined adjacent two points of time as the period required for one step in the walking movement (step S24).

The calculated period required for one step in the walking movement may be stored in a storage unit (for example, memory 2).

As described above, according to the measurement apparatus 100 in the embodiment, first, points of time closer to the points of time when a foot of the user landed are determined based on the continuous change of the vertical direction acceleration detected by the first sensor 3a. Based on the determined points of time and the travel direction acceleration detected by the second sensor 3b, the points of time when a foot of the user landed are determined. Based on the determined points of time when a foot of the user landed, the period required for one step in the traveling movement is calculated. This utilizes the existence of point of time t2 when the travel direction acceleration takes a local minimum for every step by the repeated operation of bringing force toward the opposite direction to the travel direction by landing of each left and right foot during the running movement and thereafter increasing the travel direction acceleration. Furthermore, as described above, by determining points of time closer to the points of time when a foot of the user landed by using the X axis acceleration data ACCX first, it is possible to determine the local minimum corresponding to the point of time when a foot of the user landed among the plurality of local minimums in the Y axis acceleration data ACCY existing within a time interval between adjacent two points of time t1. Accordingly, even in a case in which the waveform detected by the acceleration detecting unit 3 is complicated due to the higher running speed, the period required for one step in the running movement can be measured with high accuracy.

In a case in which the change in travel direction acceleration is equal to or less than the predetermined judgment value as in the walking movement, it is possible to calculate the period required for one step in the walking movement with high accuracy only based on the continuous change of vertical direction acceleration. That is, since the waveform of walking movement detected by the acceleration detecting unit 3 is not so complicated as the running movement, the period required for one step can be measured with high accuracy by a method which is more simplified than that of running movement.

The present invention is not limited to the above embodiment and various improvement and design changes may be performed within the scope of the present invention.

In the embodiment, the step period calculation unit 4f calculates the period required for one step in the walking movement; however, the present invention may have any configuration as long as at least the period required for one step during running movement is calculated.

The configuration of measurement apparatus 100 illustrated in the embodiment is an example, and the present invention is not limited to this.

In the embodiment, when the measurement apparatus 100 is worn by a user, the acceleration detecting unit 3 detects an upward vertical direction acceleration as a positive value, and detects a travel direction acceleration directed from a back side toward a stomach side of the user as a positive value; however, the present invention is not limited to this. While worn by the user, the acceleration detecting unit 3 may detect a vertical direction acceleration directed upward as a negative value or detect a travel direction acceleration directed from a back side toward a stomach side of the user as a negative value. In either case, the processing may be performed by providing opposite signs of positive negative signs to the acceleration values in respective directions detected by the acceleration detecting unit 3.

In such case where the acceleration detecting unit 3 detects the upward vertical direction acceleration as a negative value or travel direction acceleration directed from back side toward a stomach side of the user as a negative value, when the acceleration values in the respective directions detected by the acceleration detecting unit 3 are used without change, basically, the "local maximums" and the "local minimums" in the embodiment may be reversed to each other to reverse "positive" and "negative".

For example, if the change judgment unit 4c judges that the change in the travel direction acceleration is larger than the predetermined judgment value, the processing may be performed as follows. That is, the X axis extreme value determination unit 4d may determine, in the X axis acceleration data ACCX, points of time t0 when the acceleration value is a predetermined reference value −th1 and the waveform takes a "negative" slope, and with respect to each of the plurality of determined points of time t0, the X axis extreme value determination unit 4d may search toward the positive direction of time axis from each points of time t0 and determine the point of time t1 when the vertical direction acceleration takes an extreme value (local minimum). The Y axis extreme value determination unit 4e may search toward the negative direction of time axis from each of the points of time t1 based on the respective plurality of points of time t1 when the acceleration takes an extreme value determined by the X axis extreme value determination unit 4d in the Y axis acceleration data ACCY and determine each of the points of time t2 when the travel direction acceleration value is "positive" and takes a local maximum for the first time as the point of time when a foot of the user landed. The step period calculation unit 4f may calculate a time interval between adjacent two points of time t2 as the period required for one step in the running movement based on the points of time t2 when the travel direction acceleration takes an extreme value determined by the Y axis extreme value determination unit 4e as "step boundary".

On the other hand, if the variation judging unit 4c judges that the change in the travel direction acceleration is equal to or less than the predetermined judgment value, the step period calculation unit 4f may determine, as a "step boundary", each of the points of time when the acceleration value is the predetermined reference value and the waveform takes a "negative" slope in the X axis acceleration data ACCX and calculate the time interval between the determined adjacent two points of time as the period required for one step in the walking movement.

In the embodiment, the acceleration value detected by the acceleration detecting unit 3 is used without correction; however, the present invention is not limited to this. For example, in a case in which the measurement apparatus 100 includes an angular velocity sensor (not shown in the drawings) axial correction may be executed with respect to the acceleration value detected by the acceleration detecting unit 3. Since the measurement apparatus 100 (acceleration detecting unit 3) worn around the trunk of a human body (user) is influenced by the swing or inclination of upper body during exercise such as running, difference is generated between the axis of vertical direction and the axis of X axis acceleration of the acceleration detecting unit 3 in some cases. In such case, correction may be performed to compensate the difference component of the axial directions which are different for each time based on the angular velocity acquired by the angular velocity sensor.

Specifically, in the axial correction processing, the central control unit 1 first estimates gravity direction of each time based on angular velocity values acquired by the angular velocity sensor. The central control unit 1 corrects the acceleration value by rotating each of the acceleration axes so that the estimated gravity direction matches the X axis direction of the acceleration detecting unit 3. In the modification example, the corrected acceleration value may be used for the above-mentioned smoothing (step S12).

In addition, the above embodiment has a configuration in which the first sensor 3a, second sensor 3b, Y axis extreme value determination unit 4e and step period calculation unit 4f are driven as the first sensor, second sensor, first determination unit and the first acquiring unit under control of the central control unit 1; however, the present invention is not limited to this. The present invention may have a configuration in which the above functions are achieved by the CPU of the central control unit 1 executing programs and such like.

That is, programs including first detection routine, second detection routine, determination routine and calculation routine are stored in a grogram memory (not shown in the drawings) for storing programs. Then, the first detection routine may make the CPU of central control unit 1 function as a unit for detecting continuously the vertical direction acceleration generated in accordance with the user's traveling movement. The second detection routine may make the CPU of the central control unit 1 function as a unit for detecting continuously the travel direction acceleration generated in accordance with the user's traveling movement. The determination routine may make the CPU of the central control unit 1 function as a unit for determining the landing point of time when a foot of the user landed based on the detected continuous change of vertical direction acceleration and detected travel direction acceleration. The first acquiring routine may make the CPU of the central control unit function as a unit for acquiring the period required for one step in the traveling movement based on the determined landing points of time, each being a point of time when a foot of the user landed.

Similarly, the functions of second acquiring unit and second determination unit may also be achieved by the CPU of central control unit 1 executing programs or such like.

Furthermore, as a computer readable medium storing programs for executing each of the above processing, a non-volatile memory such as a flash memory and a portable recording medium such as a CD-ROM can also be applied as well as the ROM and a hard disk. As a medium providing program data via a communication line, carrier wave can also be applied.

Though several embodiments of the present invention have been described above, the scope of the present invention is not limited to the above embodiments, and includes the scope of inventions, which is described in the scope of claims, and the scope equivalent thereof.

What is claimed is:

1. A measurement apparatus comprising:
a judgement unit which judges whether a traveling movement of a user is a running movement or a walking movement,
a first sensor which continuously acquires a vertical direction acceleration generated in accordance with the traveling movement of the user,
a second sensor which continuously acquires a travel direction acceleration generated in accordance with the traveling movement, and
a first determination unit which determines a plurality of landing points of time each being a point of time when a foot of the user lands based on a continuous change of the vertical direction acceleration and the travel direction acceleration when the judgement unit judges that the traveling movement of the user is the running movement, and which determines the plurality of landing points of time based on only the continuous change of the vertical direction acceleration between the continuous change of the vertical direction acceleration and the travel direction acceleration when the judgement unit judges that the traveling movement of the user is the walking movement.

2. The measurement apparatus according to claim 1, further comprising:
a first acquiring unit which acquires a change in the travel direction acceleration,
wherein the judgement unit judges that the traveling movement of the user is the running movement in a case in which the change in the travel direction acceleration is larger than a first predetermined value, and the judgement unit judges that the traveling movement of the user is the walking movement in a case in which the change in the travel direction acceleration is equal to or smaller than the first predetermined value.

3. The measurement apparatus according to claim 1, further comprising:
a second determination unit which determines, based on the continuous change of the vertical direction acceleration, a plurality of taking extreme value points of time each being a point of time where the vertical direction acceleration takes an extreme value,
wherein the first determination unit determines the plurality of landing points of time based on the plurality of taking extreme value points of time.

4. The measurement apparatus according to claim 3, wherein, in a case in which an upward direction of the vertical direction is positive, the second determination unit searches along a waveform showing the continuous change of the vertical direction acceleration toward a positive direction of a time axis from each of a plurality of taking positive slope points of time each being a point of time where the waveform showing the continuous change of the vertical direction acceleration takes a positive slope and the vertical acceleration is a second predetermined value, and the second determination unit determines a plurality of points of time each being a point of time where the vertical direction acceleration takes a local maximum as the plurality of taking extreme value points of time.

5. The measurement apparatus according to claim 3, wherein, in a case in which a downward direction of the vertical direction is positive, the second determination unit searches along a waveform showing the continuous change of the vertical direction acceleration toward a positive direction of a time axis from each of a plurality of taking positive slope points of time each being a point of time where the waveform showing the continuous change of the vertical direction acceleration takes a negative slope and the vertical direction acceleration is a second predetermined value, and the second determination unit determines a plurality of points of time each being a point of time where the vertical direction acceleration takes a local minimum as the plurality of taking extreme value points of time.

6. The measurement apparatus according to claim 3, wherein, when the judgement unit judges that the traveling movement of the user is the running movement, the first determination unit searches along a waveform showing a continuous change of the travel direction acceleration toward a negative direction of a time axis from each of the taking extreme value points of time, and finds a plurality of points of time each being a point of time where the travel direction acceleration takes an extreme value for the first time to determine the points of time as the plurality of landing points of time.

7. The measurement apparatus according to claim 3, wherein, when the judgement unit judges that the traveling movement of the user is the running movement, in a case in which a forward direction of the travel direction is positive, the first determination unit searches along a waveform showing a continuous change of the travel direction acceleration toward a negative direction of a time axis from each of the taking extreme value points of time, and finds a plurality of points of time each being a point of time where the travel direction acceleration takes a negative extreme value for the first time to determine the points of time as the plurality of landing points of time.

8. The measurement apparatus according to claim 3, wherein, when the judgement unit judges that the traveling movement of the user is the running movement, in a case in which a backward direction of the travel direction is positive, the first determination unit searches along a waveform showing a continuous change of the travel direction acceleration toward a negative direction of a time axis from each of the taking extreme value points of time, and finds a plurality of points of time each being a point of time where the travel direction acceleration takes a positive extreme value for the first time to determine the points of time as the plurality of landing points of time.

9. The measurement apparatus according to claim 3, wherein, when the judgement unit judges that the traveling movement of the user is the running movement, in a case in which an upward direction of the vertical direction is positive, the first determination unit determines, as the plurality of landing points of time, a plurality of taking positive slope points of time each being a point of time where a waveform showing the continuous change of the vertical direction acceleration takes a positive slope and the vertical direction acceleration is a second predetermined value.

10. The measurement apparatus according to claim 3, wherein, when the judgement unit judges that the traveling movement of the user is walking movement, in a case in which a downward direction of the vertical direction is positive, the first determination unit determined, as the plurality of landing points of time, a plurality of taking positive slope points of time each being a point of time where a waveform showing the continuous change of the vertical direction acceleration takes a negative slope and the vertical direction acceleration is a second predetermined value.

11. A measurement method comprising:
   judging whether a traveling movement of a user is a running movement or a walking movement,
   acquiring continuously a vertical direction acceleration generated in accordance with the traveling movement of the user,
   acquiring continuously a travel direction acceleration generated in accordance with the traveling movement,
   determining a plurality of landing points of time each being a point of time when a foot of the user lands based on a continuous change of the acquired vertical direction acceleration and the travel direction acceleration when judging that the traveling movement of the user is the running movement, and determining the plurality of landing points of time based on only the continuous change of the vertical direction acceleration between the continuous change of the vertical direction acceleration and the travel direction acceleration when judging that the traveling movement of the user is the walking movement.

12. A non-transitory computer readable recording medium which stores an executable program that is read by a computer to make a controlling unit execute operations comprising:
   judging whether a traveling movement of a user is a running movement or a walking movement,
   acquiring continuously a vertical direction acceleration generated in accordance with a traveling movement of a user,
   acquiring continuously a travel direction acceleration generated in accordance with the traveling movement,
   determining, based on a continuous change of the acquired vertical direction acceleration and the travel direction acceleration, a plurality of landing points of time each being a point of time when a foot of the user lands based on a continuous change of the acquired vertical direction acceleration and the travel direction acceleration when judging that the traveling movement of the user is the running movement, and determining the plurality of landing points of time based on only the continuous change of the vertical direction acceleration between the continuous change of the vertical direction acceleration and the travel direction acceleration when judging that the traveling movement of the user is the walking movement.

13. The measurement apparatus according to claim 1, further comprising an acquiring unit which acquires a time interval between a first landing point of time among the plurality of landing points of time and a second landing point of time that is adjacent to the first landing point of time as a period required for one step in the traveling movement.

* * * * *